(12) United States Patent
Fu et al.

(10) Patent No.: US 12,398,138 B2
(45) Date of Patent: Aug. 26, 2025

(54) FGFR INHIBITOR COMPOUND IN SOLID FORM AND PREPARATION METHOD THEREFOR

(71) Applicant: CSPC ZHONGQI PHARMACEUTICAL TECHNOLOGY (SHIJIAZHUANG) CO., LTD., Hebei (CN)

(72) Inventors: Zhifei Fu, Shanghai (CN); Miaorong Luo, Shanghai (CN); Jikui Sun, Shanghai (CN); Yang Zhang, Shanghai (CN); Jian Li, Shanghai (CN); Shuhui Chen, Shanghai (CN)

(73) Assignee: CSPC ZHONGQI PHARMACEUTICAL TECHNOLOGY (SHIJIAZHUANG) CO., LTD., Hebei (CN)

( * ) Notice: Subject to any disclaimer, the term of this patent is extended or adjusted under 35 U.S.C. 154(b) by 1046 days.

(21) Appl. No.: 17/310,610

(22) PCT Filed: Feb. 14, 2020

(86) PCT No.: PCT/CN2020/075322
§ 371 (c)(1),
(2) Date: Aug. 13, 2021

(87) PCT Pub. No.: WO2020/164603
PCT Pub. Date: Aug. 20, 2020

(65) Prior Publication Data
US 2022/0177475 A1    Jun. 9, 2022

(30) Foreign Application Priority Data
Feb. 15, 2019   (CN) .......................... 201910117530.7

(51) Int. Cl.
C07D 487/04    (2006.01)
A61K 31/53     (2006.01)
A61P 35/00     (2006.01)

(52) U.S. Cl.
CPC ............ *C07D 487/04* (2013.01); *A61P 35/00* (2018.01); *A61K 31/53* (2013.01); *C07B 2200/13* (2013.01)

(58) Field of Classification Search
None
See application file for complete search history.

(56) References Cited

U.S. PATENT DOCUMENTS

2013/0158000 A1    6/2013  Brohm et al.
2015/0031676 A1    1/2015  Lobell et al.
2015/0080371 A1    3/2015  Collin et al.
2016/0136168 A1    5/2016  Sootome
2020/0207773 A1    7/2020  Wang et al.

FOREIGN PATENT DOCUMENTS

| CN | 104136439 | 11/2014 | |
| CN | 104159900 | 11/2014 | |
| CN | 104245700 | 12/2014 | |
| EP | 3670513 A1 | 6/2020 | |
| JP | 2015-500307 A | 1/2015 | |
| JP | 2015-508087 A | 3/2015 | |
| JP | WO2015008844 | 3/2017 | |
| JP | 2020-532500 A | 11/2020 | |
| WO | WO 2013/087647 | 6/2013 | |
| WO | WO 2013/124316 | 8/2013 | |
| WO | WO 2019/034076 | 2/2019 | |
| WO | WO-2019034076 A1 * | 2/2019 | ............. A61K 31/53 |

OTHER PUBLICATIONS

Collin et al. (2018), Discovery of Rogaratinib (BAY 1163877): a pan-FGFR Inhibitor, Chem Med Chem, 13, 437-445. (Year: 2018).*
English translation of WO2019034076 (Year: 2019).*
English translation of PCT International Search Report issued in International Application No. PCT/CN2020/075322, dated May 15, 2020.
English translation of Japanese Office Action issued in Application No. 2021-547542, dated Mar. 24, 2023.

* cited by examiner

*Primary Examiner* — Juliet C Switzer
*Assistant Examiner* — Dawanna Shar-Day White
(74) *Attorney, Agent, or Firm* — Parker Highlander PLLC

(57) ABSTRACT

Disclosed are the solid form, crystalline form, crystal form A of a compound of formula (I), and a preparation method therefor, crystal form B and a preparation method therefor. Also disclosed are use of the solid form, crystalline form, crystal form A, and crystal form B in the preparation of drugs for the treatment of diseases related to FGFR.

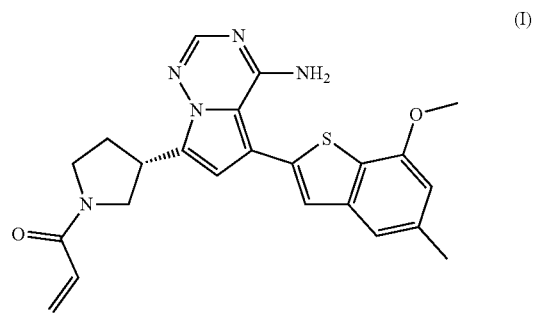

(I)

3 Claims, 4 Drawing Sheets

FGFR INHIBITOR COMPOUND IN SOLID FORM AND PREPARATION METHOD THEREFOR

This application is a national phase application under 35 U.S.C. § 371 of International Application No. PCT/CN2020/075322, filed on Feb. 14, 2020, which claims the priority to Chinese Patent Application No. 201910117530.7, titled "CRYSTAL FORM OF FGFR INHIBITOR AND PREPARATION METHOD THEREFOR", filed on Feb. 15, 2019 with the China National Intellectual Property Administration, the entirety of each of which is incorporated herein by reference.

FIELD OF THE INVENTION

The present disclosure relates to a solid form, crystalline form, crystal form A and crystal form B of a compound of Formula (I), as well as preparation method of the crystal form A and crystal form B, and further relates to use of the solid form, crystalline form, crystal form A, crystal form B in the manufacture of a medicament for treating FGFR-related diseases.

BACKGROUND OF THE INVENTION

Fibroblast growth factor receptor (FGFR) is a receptor of fibroblast growth factor (FGF) for signal transduction, which belongs to the family consists of four members (FGFR1, FGFR2, FGFR3, FGFR4), and is a glycoprotein composed of an extracellular immunoglobulin (Ig)-like domain, a hydrophobic transmembrane domain and an intracellular part including a tyrosine kinase domain. Through the receptor (FGFR), fibroblast growth factor (FGF) exerts its important effects in many physiological regulations such as cell proliferation, cell differentiation, cell migration and angiogenesis. And, it has been demonstrated by many evidences that the abnormality of FGF signaling pathways (e.g., high expression, gene amplification, gene mutation, chromosomal recombination) is directly associated with many pathological processes such as the proliferation, migration, invasion and angiogenesis of tumor cells. Therefore, FGFR has become an important therapeutic target, attracting a wide interest in research.

WO2015008844 reported a series of compounds having inhibitory activity against FGFR, including reference compound 1 and 2. WO 2013124316, WO 2013087647, and US 20130158000 also reported a series of compounds with inhibitory activity against FGFR, including the benzothiophene structure in the present disclosure, and reference compound 3.

Reference compound 1

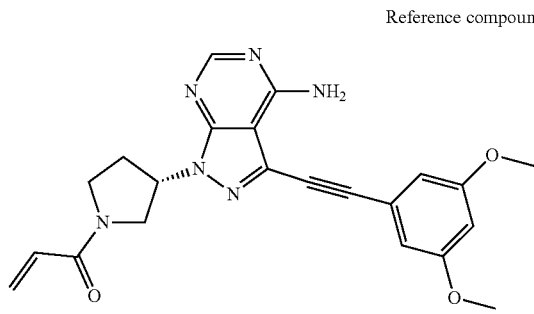

Reference compound 2

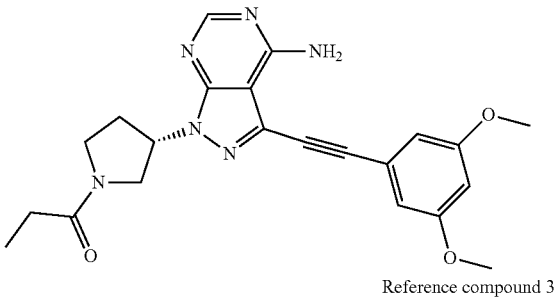

Reference compound 3

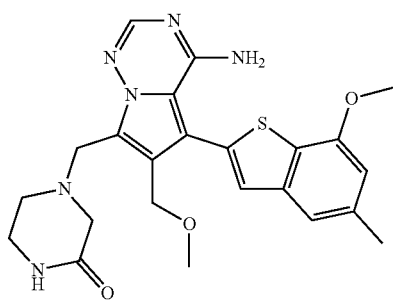

WO 2019034076 discloses a class of compounds with inhibitory activity against FGFR, including compound WX001 (including a pair of WX001A and WX001B as optical isomers) with good activity, but it was failed to obtain its solid form product.

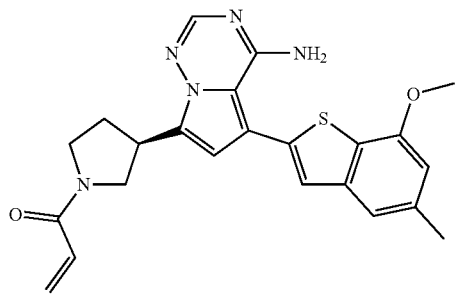

WX001A or WX001B

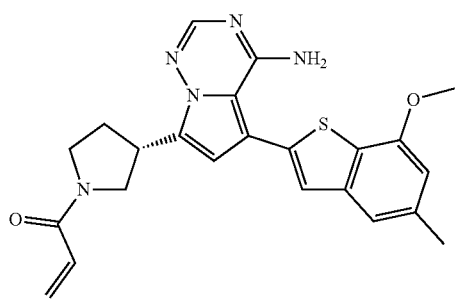

WX001A or WX001B

The present inventors also found that it is difficult to obtain a solid form of compound WX001 by conventional methods, such as using methanol, ethanol, tetrahydrofuran as a solvent under conventional processing conditions.

Therefore, the problem to be solved is to obtain the compound WX001A or WX001B in solid form, so as to provide products convenient for manufacture, purification, storage and use.

SUMMARY OF THE INVENTION

The present inventors unexpectedly found a method capable of obtaining the compound WX001A or WX001B described above in solid form, and further obtained the corresponding product in solid and further crystal form.

Based on the above findings, in the first aspect, the present disclosure provides a compound represented by Formula (I) in solid form, (I)

In the second aspect, the present disclosure provides the compound represented by Formula (I) in a crystalline form.

In a preferred aspect, the present disclosure provides a crystal form A of the compound represented by Formula (I) with diffraction peaks at a 2θ angle of 6.37±0.2°, 9.90±0.2°, and 19.07±0.2° in an X-ray powder diffraction pattern thereof.

In some embodiments of the present disclosure, the described crystal form A of the compound represented by Formula (I) has diffraction peaks at a 2θ angle of 6.37±0.2°, 9.90±0.2°, 12.74±0.2°, 13.35±0.2°, 14.26±0.2°, 16.31±0.2°, 19.07±0.2°, and 21.83±0.2° in an X-ray powder diffraction pattern thereof.

In some embodiments of the present disclosure, the described crystal form A of the compound represented by Formula (I) has an XRPD pattern as shown in FIG. 1.

In some embodiments of the present disclosure, the described crystal form A of the compound represented by Formula (I) has an XRPD pattern analysis data as shown in Table 1.

TABLE 1 the XRPD pattern analysis data of the crystal form A of the compound represented by Formula (I)

| NO. | 2θ angle (°) | D-spacing (Å) | relative intensity (%) |
|---|---|---|---|
| 1 | 6.367 | 13.8715 | 100.0 |
| 2 | 6.743 | 13.0975 | 26.7 |
| 3 | 9.898 | 8.9285 | 19.2 |
| 4 | 12.736 | 6.9451 | 21.9 |
| 5 | 13.352 | 6.6257 | 12.4 |
| 6 | 14.257 | 6.2072 | 31.4 |
| 7 | 15.247 | 5.8061 | 3.3 |
| 8 | 15.734 | 5.6275 | 3.6 |
| 9 | 16.310 | 5.4303 | 8.8 |
| 10 | 17.111 | 5.1776 | 4.6 |
| 11 | 19.070 | 4.6501 | 33.4 |

TABLE 1-continued the XRPD pattern analysis data of the crystal form A of the compound represented by Formula (I)

| NO. | 2θ angle (°) | D-spacing (Å) | relative intensity (%) |
|---|---|---|---|
| 12 | 20.264 | 4.3786 | 4.5 |
| 13 | 20.909 | 4.2450 | 4.3 |
| 14 | 21.339 | 4.1604 | 6.5 |
| 15 | 21.833 | 4.0675 | 11.2 |
| 16 | 22.165 | 4.0073 | 6.6 |
| 17 | 23.513 | 3.7805 | 4.6 |
| 18 | 24.490 | 3.6318 | 4.0 |
| 19 | 25.345 | 3.5111 | 3.7 |
| 20 | 25.972 | 3.4279 | 11.2 |
| 21 | 26.904 | 3.3112 | 7.4 |
| 22 | 28.180 | 3.1640 | 3.7 |
| 23 | 28.633 | 3.1150 | 6.0 |

In some embodiments of the present disclosure, the described crystal form A of the compound represented by Formula (I) has an endothermic peak at 141.05° C.±5° C. in a differential scanning calorimetry curve thereof.

In some embodiments of the present disclosure, the described crystal form A of the compound represented by Formula (I) has a DSC curve as shown in FIG. 2.

In some embodiments of the present disclosure, the described crystal form A of the compound represented by Formula (I) has a weight loss of 1.232% at 124.65±3° C. in a thermogravimetric analysis pattern thereof.

In some embodiments of the present disclosure, the described crystal form A of the compound represented by Formula (I) has a TGA pattern as shown in FIG. 3.

The present disclosure further provides a method for preparing the described crystal form A of the compound represented by Formula (I), comprising:

(a) adding a compound represented by Formula (I) into a nitrile solvent or an ester solvent;

(b) stirring at 30-50° C. for 40-55 hours; and (c) separating out the crystal form A of the compound represented by Formula (I).

In the above method, the separation in step (c) can be performed by centrifugation, filtration, etc., and preferably by centrifugation; and optionally, the separation in step (c) can be followed by drying.

In some embodiments of the present disclosure, the nitrile solvent described above is selected from acetonitrile, propionitrile and butyronitrile.

In some embodiments of the present disclosure, the ester solvent described above is selected from ethyl acetate, methyl acetate, isopropyl acetate and ethyl formate.

In another aspect, the present disclosure further provides a crystal form B of the compound represented by Formula (I) with diffraction peaks at a 2θ angle of 3.60±0.2°, 9.14±0.2°, and 15.07±0.2° in an X-ray powder diffraction pattern thereof.

The crystal form B of the compound represented by Formula (I) provided by the present disclosure has diffraction peaks at a 2θ angle of 9.14±0.2°, and 15.07±0.2° in an X-ray powder diffraction pattern thereof.

In some embodiments of the present disclosure, the described crystal form B of the compound represented by Formula (I) has diffraction peaks at a 2θ angle of 3.60±0.2°, 9.14±0.2°, 11.05±0.2°, 13.25±0.2°, 15.07±0.2°, 16.47±0.2°, 18.31±0.2°, and 22.29±0.2° in an X-ray powder diffraction pattern thereof.

In some embodiments of the present disclosure, the described crystal form B of the compound represented by Formula (I) has diffraction peaks at a 2θ angle of 9.14±0.2°, 11.05±0.2°, 13.25±0.2°, 15.07±0.2°, 16.47±0.2°, 18.31±0.2°, and 22.29±0.2° in an X-ray powder diffraction pattern thereof.

In some embodiments of the present disclosure, the described crystal form B of the compound represented by Formula (I) has an XRPD pattern as shown in FIG. 4.

In some embodiments of the present disclosure, the described crystal form B of the compound represented by Formula (I) has an XRPD pattern analysis data as shown in Table 2.

TABLE 2 the XRPD pattern analysis data of the crystal form B of the compound represented by Formula (I)

| NO. | 2θ angle (°) | D-spacing (Å) | relative intensity (%) |
|---|---|---|---|
| 1 | 3.601(baseline) | 24.5168 | 45.8 |
| 2 | 9.138 | 9.6695 | 100.0 |
| 3 | 11.050 | 8.0006 | 11.5 |
| 4 | 12.449 | 7.1045 | 3.5 |
| 5 | 13.254 | 6.6748 | 6.3 |
| 6 | 15.070 | 5.8739 | 25.5 |
| 7 | 15.445 | 5.7323 | 7.9 |
| 8 | 16.468 | 5.3783 | 4.2 |
| 9 | 18.309 | 4.8415 | 19.9 |
| 10 | 19.565 | 4.5334 | 4.6 |
| 11 | 22.290 | 3.9850 | 18.8 |
| 12 | 23.142 | 3.8402 | 4.1 |
| 13 | 26.047 | 3.4181 | 2.9 |
| 14 | 27.102 | 3.2874 | 2.8 |
| 15 | 27.613 | 3.2278 | 5.7 |
| 16 | 28.325 | 3.1482 | 3.3 |
| 17 | 30.653 | 2.9142 | 5.8 |
| 18 | 19.565 | 4.5334 | 4.6 |

In some embodiments of the present disclosure, the described crystal form B of the compound represented by Formula (I) has an endothermic peak with a start point at 174.09° C.±5° C. in a differential scanning calorimetry curve thereof.

In some embodiments of the present disclosure, the described crystal form B of the compound represented by Formula (I) has a DSC curve as shown in FIG. 5.

In some embodiments of the present disclosure, the described crystal form B of the compound represented by Formula (I) has a weight loss of 0.4324% at 169.70±3° C. in a thermogravimetric analysis pattern thereof.

In some embodiments of the present disclosure, the described crystal form B of the compound represented by Formula (I) has a TGA pattern as shown in FIG. 6.

The present disclosure further provides a method for preparing the described crystal form B of the compound represented by Formula (I), comprising:

(a) adding the crystal form A of the compound represented by Formula (I) into an alcohol solvent or a mixed solvent of an alcohol solvent and water;

(b) stirring at 30-50° C. for 5-30 hours;

(c) standing at 10-20° C. for 3-10 hours; and (d) separating out the crystal form B of the compound represented by Formula (I).

In the above-described method, the separation in step (d) can be performed by centrifugation, filtration, etc, and preferably by centrifugation; and optionally, the separation in step (d) can be followed by drying.

In some embodiments of the present disclosure, the described alcohol solvent is selected from methanol, ethanol and isopropanol.

In some embodiments of the present disclosure, the described mixed solvent of an alcohol solvent and water is selected from a mixed solvent of methanol and water, a mixed solvent of ethanol and water, and a mixed solvent of isopropanol and water.

The present disclosure further provides use of the compound represented by Formula (I) in solid form described above, the compound represented by Formula (I) in a crystalline form, the crystal form A of the compound represented by Formula (I), the crystal form B of the compound represented by Formula (I) in the manufacture of a medicament for treating FGFR-related diseases.

In some embodiments of the present disclosure, the described FGFR-related disease is a solid tumor.

Technical Effect

The crystal form B of the compound of Formula (I) has a weight gain caused by moisture-adsorption of 0.1928% at 25° C. and 80% RH, showing no or almost no hygroscopicity, and indicating a good prospects for making medicaments. The compound of Formula (I) exhibited a good inhibitory activity against wild-type FGFR, and also a good inhibitory activity against mutant-type FGFR, and had good pharmacokinetic indices.

Definition and Description

Unless stated otherwise, the following terms or phrases used herein are intended to have the meanings defined below. A particular term or phrase undefined specifically should be understood in accordance with its ordinary meaning rather than be considered uncertain or unclear. When a trade name appears herein, it is intended to refer to its corresponding commodity or its active ingredient.

The intermediate compounds of the present disclosure can be prepared by a variety of synthetic methods well-known to those skilled in the art, including the specific embodiments given below, the embodiments formed by these specific embodiments in combination with other chemical synthesis methods, as well as its equivalent alternative methods well-known to those skilled in the art. The preferred embodiments include, but are not limited to, the examples of the present disclosure.

The solvents used in the present disclosure are commercially available and can be used without further purification.

The present disclosure uses the following abbreviations: DMF stands for dimethylformamide; MsOH stands for methanesulfonic acid; EtOH stands for ethanol; NaOH stands for sodium hydroxide; DMSO stands for dimethyl sulfoxide.

Compounds are named manually or by ChemDraw® software, and commercially available compounds use the supplier catalog name.

X-Ray Powder Diffraction (XRPD) Method in the Present Disclosure

Instrument model: Bruker D8 advance X-ray diffractometer

Test method: Approximately 10-20 mg sample was used for XRPD detection.

The detailed XRPD parameters were as follows:
Light tube: Cu, kα, (λ=1.54056 Å).
Light tube voltage: 40 kV, Light tube current: 40 mA
Divergence slit: 0.60 mm
Detector slit: 10.50 mm
Anti-scatter slit: 7.10 mm
Scanning range: 3-40 deg Step diameter: 0.02 deg
Step length: 0.12 seconds
Rotation speed of the sample tray: 15 rpm
Differential Scanning Calorimetry (DSC) Method in the Present Disclosure
Instrument model: TA Q2000 Differential scanning calorimeter
Test method: A sample (0.5-1 mg) was placed in a DSC aluminum pot and tested at 25° C.-300° C. and 10° C./min. The heating rate of m-DSC was 2° C./min.
Thermal Gravimetric Analysis (TGA) Method in the Present Disclosure
Instrument model: TA Q5000 Thermal Gravimetric Analyzer
Test method: A sample (2-5 mg) was placed in a TGA platinum pot for testing under the condition of 25 mL/min $N_2$, and heated at a heating rate of 10° C./min from room temperature to 350° C. or until a weight loss of 20%.
Dynamic Vapor Sorption (DVS)
Test condition: Approximately 10-15 mg of sample was used for DVS detection.
Equilibrating dm/dt: 0.01%/min: (time: 10 min-180 min (maximum))
Drying: 0% RH, 120 min
RH (%) measuring gradient: 10%
Range of RH (%) measuring gradient: 0%-90%-0%
The evaluation criteria was as follows:

| hygroscopicity classification | weight gain caused by moisture-adsorption * |
|---|---|
| deliquescence | A liquid is formed due to adsorption of much of moisture. |
| very high hygroscopicity | weight gain caused by moisture is not less than 15%. |
| hygroscopicity | weight gain caused by moisture is less than 15% but not less than 2%. |
| slight hygroscopicity | weight gain caused by moisture is less than 2% but not less than 0.2%. |
| no or almost no hygroscopicity | weight gain caused by moisture is less than 0.2%. |

* weight gain caused by moisture-adsorption at 25° C. and 80% RH.

DETAILED DESCRIPTION OF THE INVENTION

Figure 1:
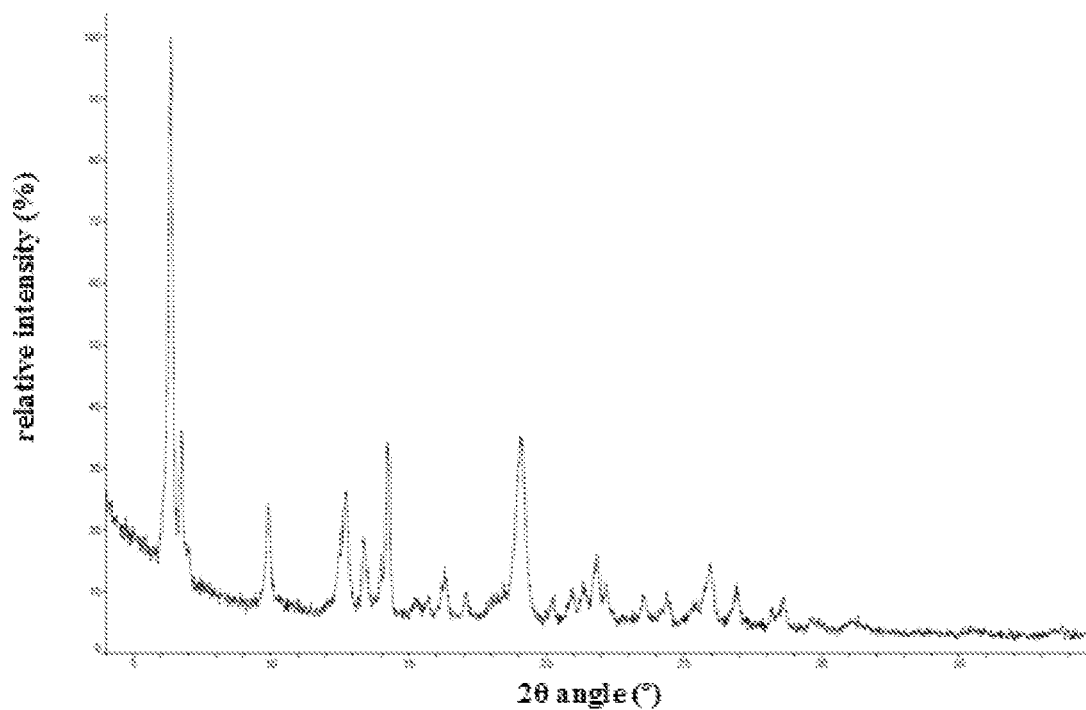
FIG. 1 is an XRPD pattern of the crystal form A of the compound of Formula (I)
Figure 2:
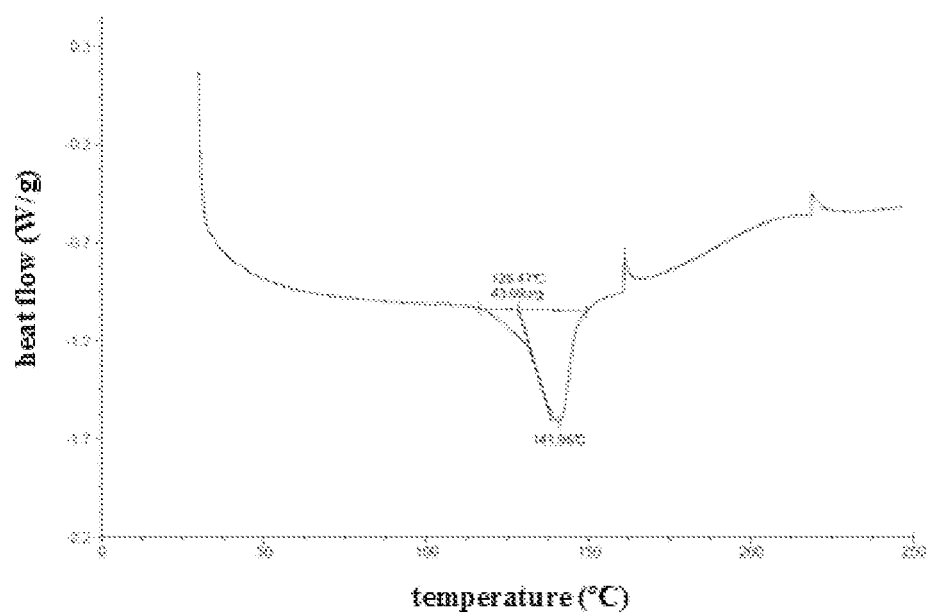
FIG. 2 is a DSC curve of the crystal form A of the compound of Formula (I)
Figure 3:
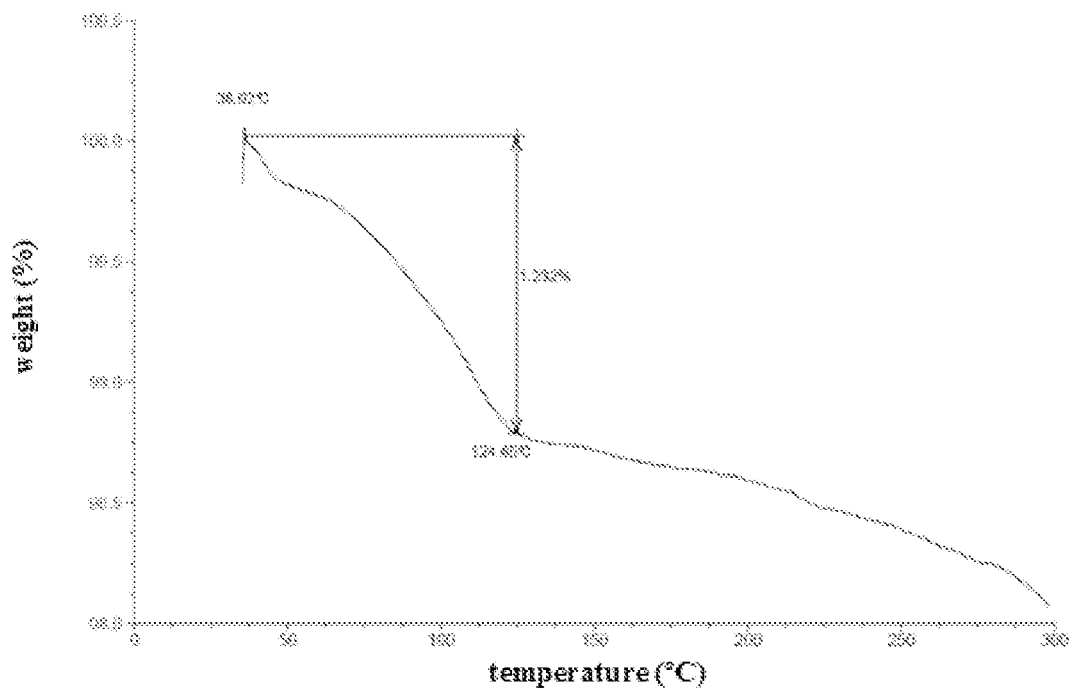
FIG. 3 is a TGA pattern of the crystal form A of the compound of Formula (I).
Figure 4:
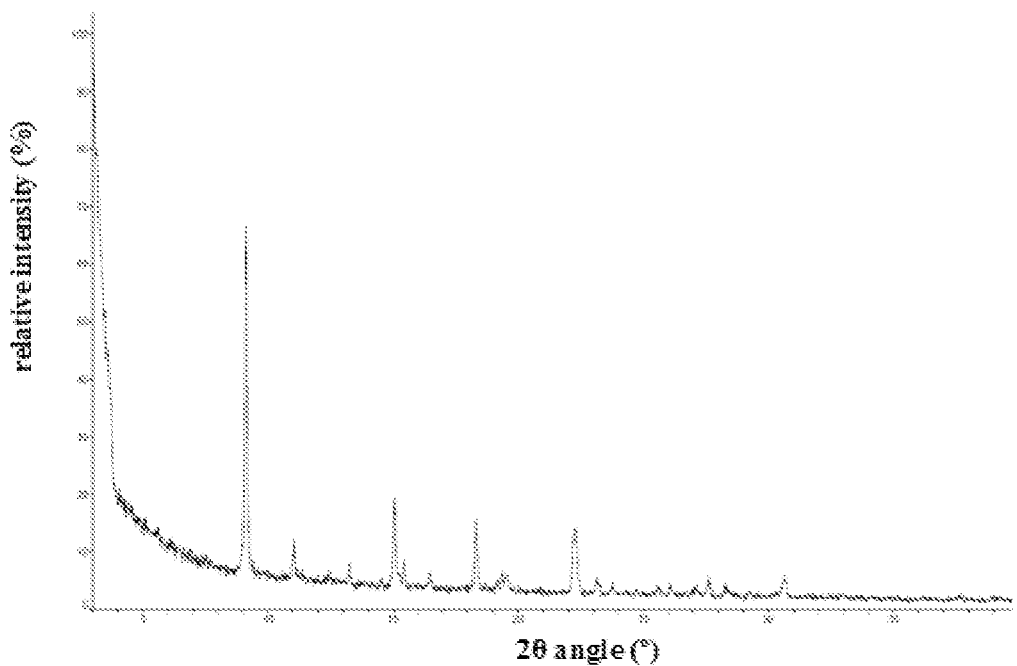
FIG. 4 is an XRPD pattern of the crystal form B of the compound of Formula (I)
Figure 5:
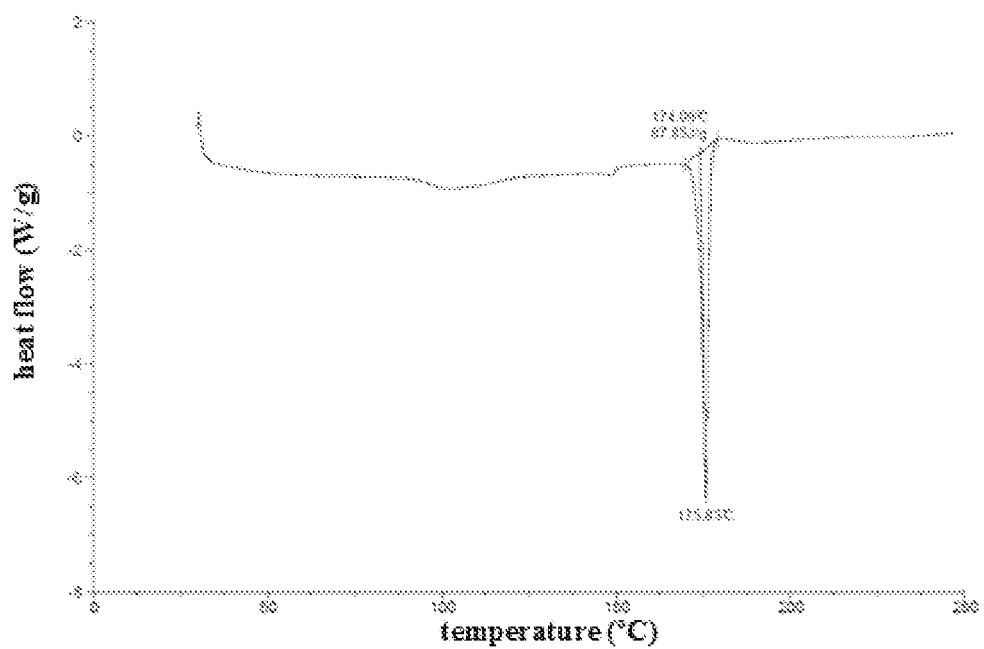
FIG. 5 is a DSC curve of the crystal form B of the compound of Formula (I)
Figure 6:
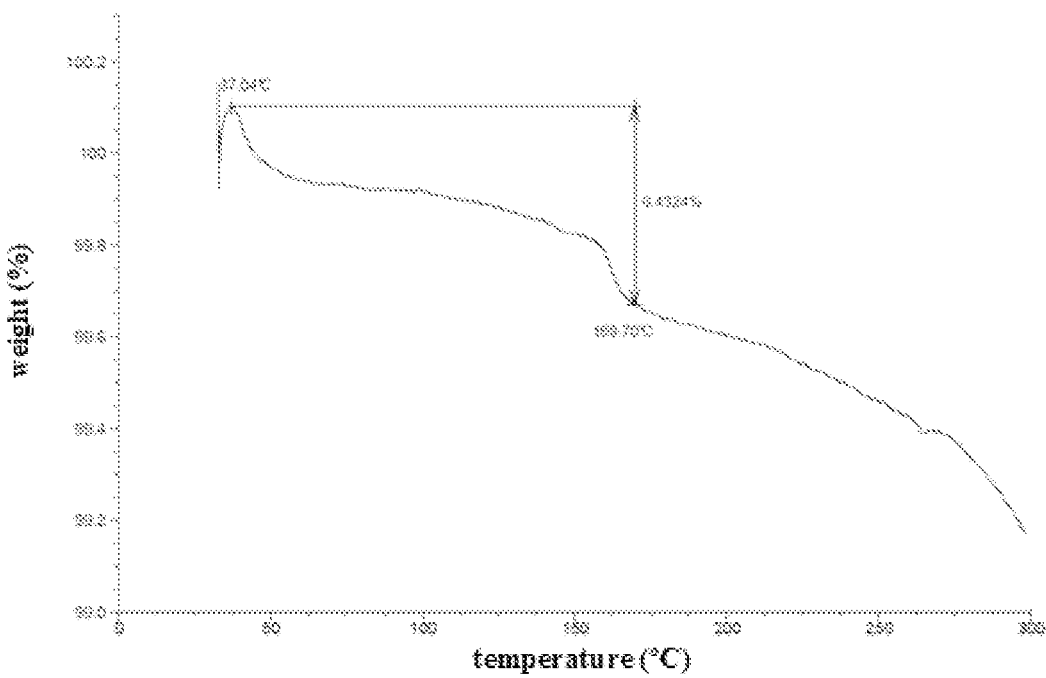
FIG. 6 is a TGA pattern of the crystal form B of the compound of Formula (I)

Hereinafter, in order to understand the contents of the present disclosure better, specific examples is given to further illustrate the contents of the present disclosure, but, they are not intended to limit the content of the present disclosure.

EXAMPLES

Intermediate A1:

Synthesis Route:

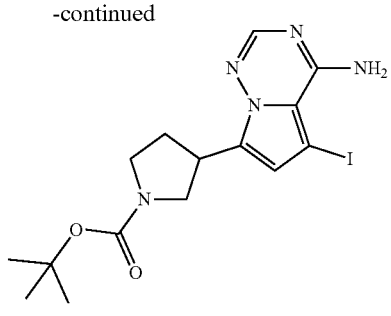

A1

Step 1: Synthesis of Compound A1-1

At room temperature, first, 4-amino-7-bromopyrrolo[1,2-f][1,2,4]triazine (3.00 g, 14.1 mmol, 1.00 eq) was dissolved in a mixed solution of 1,4-dioxane (40 mL) and water (8 mL), and then to the same mixed solution, 1-Boc-2,5-dihydro-1H-pyrrole-3-boronic acid pinacol ester (4.36 g, 14.8 mmol, 1.05 eq), potassium phosphate (8.97 g, 42.2 mmol, 3.00 eq) and [1,1'-bis(diphenylphosphino)ferrocene]dichloropalladium (1.03 g, 1.41 mmol, 0.10 eq) were added in sequence. Under the protection of nitrogen gas, the reaction solution was heated to 80° C. and stirred for 2 hours. After the completion of the reaction, the reaction solution was cooled to 25° C. and poured into 20 mL of water. A black solid was produced and collected through filtration, and then dissolved in a mixed solution of dichloromethane and methanol (100 mL, 5:1), and filtered again. The filtrate was dried with anhydrous sodium sulfate, and evaporated under reduced pressure through a rotary evaporator to remove the organic solvent, and to give a crude product. The crude product was slurried with ethyl acetate (30 mL), and filtered to give compound A1-1. LCMS (ESI) m/z: 302.1 [M+H]$^+$, $^1$H NMR (400 MHz, deuterated DMSO) δ=7.95 (s, 1H), 7.79 (brs, 2H), 6.92 (s, 1H), 6.80-6.66 (m, 2H), 4.47 (s, 2H), 4.24 (s, 2H), 1.44 (s, 9H).

Step 2: Synthesis of Compound A1-2

At room temperature, palladium hydroxide (615 mg, 438 μmol) was added to a solution of A1-1 (1.20 g, 3.98 mmol, 1.00 eq) in methanol (30 mL). After gas replacement using hydrogen gas for 3 times, the reaction solution was heated to 50° C. and stirred under 50 psi hydrogen pressure for 2 hours. The reaction solution was cooled to room temperature and filtered to remove the catalyst. The filtrate was evaporated under reduced pressure through a rotary evaporator to remove the solvent to give A1-2. $^1$H NMR (400 MHz, deuterated methanol) δ: 7.80 (s, 1H), 6.86 (d, J=4.4 Hz, 1H), 6.53 (d, J=4.4 Hz, 1H), 3.96-3.79 (m, 2H), 3.60-3.51 (m, 1H), 3.49-3.38 (m, 2H), 2.39-2.36 (m, 1H), 2.19-2.13 (m, 1H), 1.49 (d, J=3.6 Hz, 9H).

Step 3: Synthesis of Compound A1

At room temperature, iodosuccinimide (26.7 g, 119 mmol, 3.00 eq) was added in batches to a solution of A1-2 (12.0 g, 39.6 mmol, 1.00 eq) in N,N-dimethylformamide (150 mL). After the reaction solution was stirred at room temperature for 1 hour, it was slowly added into ice water (200 mL) and a solid precipitated out. After filtration, the solvent was removed and the filter cake was dried by rotary evaporation under reduced pressure to give compound A1. $^1$H NMR (400 MHz, deuterated DMSO) δ=7.88 (s, 1H), 6.75 (s, 1H), 3.77-3.68 (m, 2H), 3.42-3.38 (m, 1H), 3.28-3.23 (m, 2H), 2.31-2.22 (m, 1H), 2.05-1.98 (m, 1H), 1.39 (d, J=5.2 Hz, 9H).

Intermediate B1:

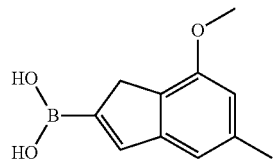

Synthesis Route:

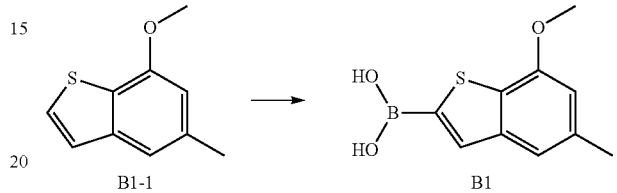

A solution of B1-1 (2.00 g, 11.22 mmol, 1.00 eq) in tetrahydrofuran (20.00 mL) was cooled to −70° C. To the cooled solution, a solution of butyl lithium in n-hexane (2.5 mol/L, 8.98 mL, 2.00 eq) was added slowly dropwise, and stirred for 1 hour after the addition. Then, triisopropyl borate (2.11 g, 11.22 mmol, 1.00 eq) was added and stirred for 1 hour after the addition. The reaction was quenched by adding water (10 mL) dropwise. The quenched reaction mixture was concentrated to remove tetrahydrofuran. The residue was washed with petroleum ether (50 mL), and then adjusted to a pH of 5 with dilute hydrochloric acid, to produce a white solid. After filtration, the filter cake was washed with water (50 mL), and then dried under vacuum to give intermediate B1. $^1$H NMR (400 MHz, deuterated chloroform) δ=7.72 (s, 1H), 7.28 (s, 1H), 6.67 (s, 1H), 4.01 (s, 3H), 2.50 (s, 3H).

Example 1 Synthesis of the Compound of Formula (I)

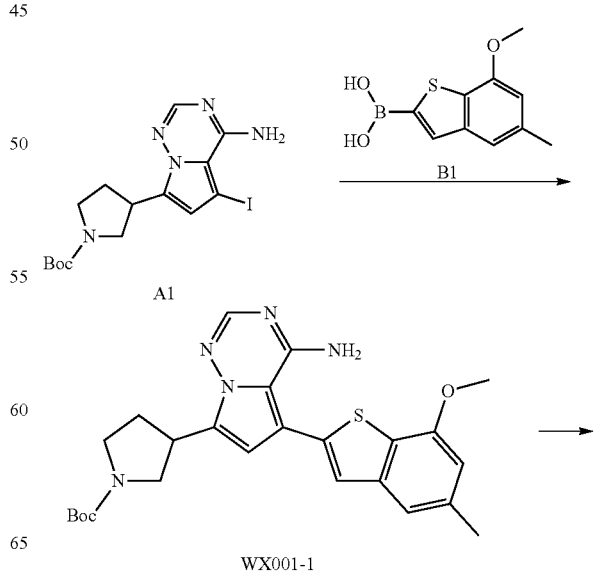

WX001-1

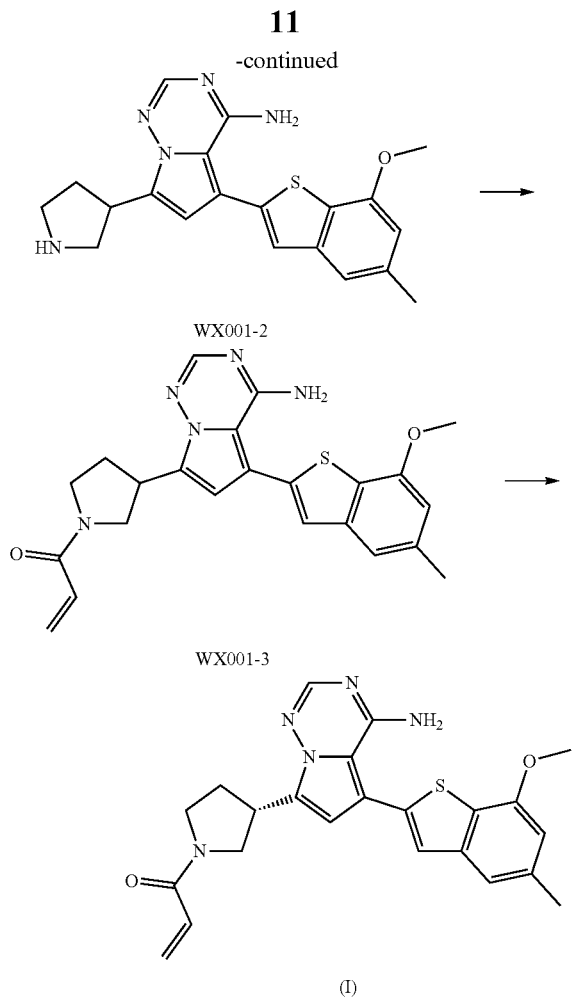

Step 1: Synthesis of Compound WX001-1

At room temperature, compound B1 (777.25 mg, 3.50 mmol, 2.50 eq), sodium carbonate (296.77 mg, 2.80 mmol, 2.00 eq) and tetrakis(triphenylphosphine)palladium (161.78 mg, 140.00 μmol, 0.10 eq) were added in sequence to a mixed solution of compound A1 (600.00 mg, 1.40 mmol, 1.00 eq) in ethylene glycol dimethyl ether (9 mL) and ethanol (3 mL) and water (0.5 mL). After gas replacement with nitrogen gas for 3 times, the mixture was heated to 90° C. After the mixture was stirred for 5 hours, it was cooled to room temperature and poured into 30 mL of water, and then extracted with dichloromethane (10 mL) for 5 times. The organic phases were combined together and dried with anhydrous sodium sulfate. After filtration, the filtrate was subjected to rotary evaporation under reduced pressure to remove solvent to give a crude product. The crude product was purified through column chromatography (petroleum ether/ethyl acetate=10/1 to 1/3) to give WX001-1. LCMS (ESI) m/z: 480.2 [M+H]$^+$, 502.2 [M+Na]$^+$, $^1$H NMR (400 MHz, deuterated methanol) δ=7.91 (s, 1H), 7.27 (s, 2H), 6.77 (s, 1H), 6.70 (s, 1H), 4.00 (s, 3H), 3.96-3.90 (m, 2H), 3.64-3.50 (m, 3H), 2.49 (s, 3H), 2.44-2.36 (m, 2H), 1.50 (s, 9H).

Step 2: Synthesis of Compound WX001-2

At room temperature, a solution of hydrochloric acid in ethyl acetate (4 mol/L, 2.00 mL, 9.51 eq) was added slowly dropwise into a solution of WX001-1 (350.00 mg, 729.79 μmol, 1.00 eq) in ethyl acetate (2 mL), and stirred for 1 hour. After filtration, a solid was obtained and dried under reduced pressure to give a hydrochloride salt of compound WX001-2. LCMS (ESI) m/z: 380.1 [M+H]$^+$, $^1$H NMR (400 MHz, deuterated methanol) δ=8.17 (s, 1H), 7.46 (s, 1H), 7.33 (s, 1H), 7.12-7.06 (m, 1H), 6.84 (s, 1H), 4.12-4.06 (m, 1H), 4.02 (s, 3H), 3.92-3.82 (m, 2H), 3.67-3.58 (m, 2H), 2.66-2.60 (m, 1H), 2.51 (s, 3H), 2.39-2.32 (m, 1H).

Step 3: Synthesis of the Compound of Formula (I)

At 0° C., diisopropylethylamine (258.56 mg, 2.00 mmol, 349.41 μL, 4.00 eq) and a solution of acryloyl chloride in dichloromethane (0.25 M, 1.80 mL, 0.90 eq) was added in sequence to a solution of the WX001-2 hydrochloric acid salt (200.00 mg, 500.16 μmol, 1.00 eq) in dichloromethane (4.00 mL), and stirred for 5 minutes. Then, the reaction liquid was poured into 2 mL of water. After layer separation, the water phase was extracted with dichloromethane (1 mL) for 3 times. The organic phases were combined together and dried with anhydrous sodium sulfate. After filtration, the filtrate was subjected to rotary evaporation under reduced pressure to remove the solvent and to give a crude product. The crude product was purified with a thin-layer preparation plate (dichloromethane/methanol=10/1) to give compound WX001-3. The compound WX001-3 was subjected to chiral resolution (column: AS (250 mm×30 mm, 5 m), mobile phase: [0.1% ammonium hydroxide, ethanol], carbon dioxide: 40%-40%) to give the compound of Formula (I) (retention time: 6.98 minutes). The retention time was measured by using an analytical column of Chiralpak AS-3 150×4.6 mm 3 μm, a mobile phase of A: carbon dioxide B: methanol (0.05% diethylamine), 40% carbon dioxide, at a flow rate of 2.5 mL/min, and a column temperature of 35° C. LCMS (ESI) m/z: 434.2 [M+H]$^+$, 456.1[M+Na]$^+$, $^1$H NMR (400 MHz, deuterated methanol) δ=7.75 (d, J=2.8 Hz, 1H), 7.08 (s, 2H), 6.61 (s, 1H), 6.54 (d, J=6.4 Hz, 1H), 6.41-6.51 (m, 1H), 6.20-6.16 (m, 1H), 5.66-5.42 (m, 1H), 4.09-3.96 (m, 1H), 3.85 (s, 3H), 3.80-3.38 (m, 4H), 2.44-2.25 (m, 4H), 2.21-1.99 (m, 1H).

Example 2: Preparation of Crystal Form A 500 mg of the compound of Formula (I) prepared in Example 1 was weighed and added into a 40 mL glass flask, then added with 8 mL of acetonitrile and a magnetic stir bar. The mixture was stirred until it became a suspension sample. The above sample was further stirred for 2 days (protected from light) on a magnetic heating stirrer (40° C.). The sample was quickly centrifuged, and the residual solid was dried under vacuum in a vacuum drying oven at 30° C. overnight to remove the residual solvent and to give a crystal form A of the compound of Formula (I).

Example 3: Preparation of Crystal Form B 600 mg of the crystal form A of the compound of Formula (I) prepared in Example 2 was weighed and added into a 40 mL glass flask, then added with 12 mL of ethanol as solvent and a magnetic stir bar. The mixture was stirred until it became a suspension sample. The above sample was further stirred overnight (protected from light) on a magnetic heating stirrer (40° C.), and allowed to stand for 5 hours at room temperature (about 15° C.). The sample was quickly centrifuged and the supernatant was removed. The solid resulted from the centrifugation was dried under vacuum in a vacuum drying oven at 40° C. for 2 hours firstly and then at 30° C. for 60 hours, to give a crystal form B of the compound of Formula (I).

Example 4: Investigation on the Hygroscopicity of the Crystal Form B of the Compound of Formula (I)

Figure 7:
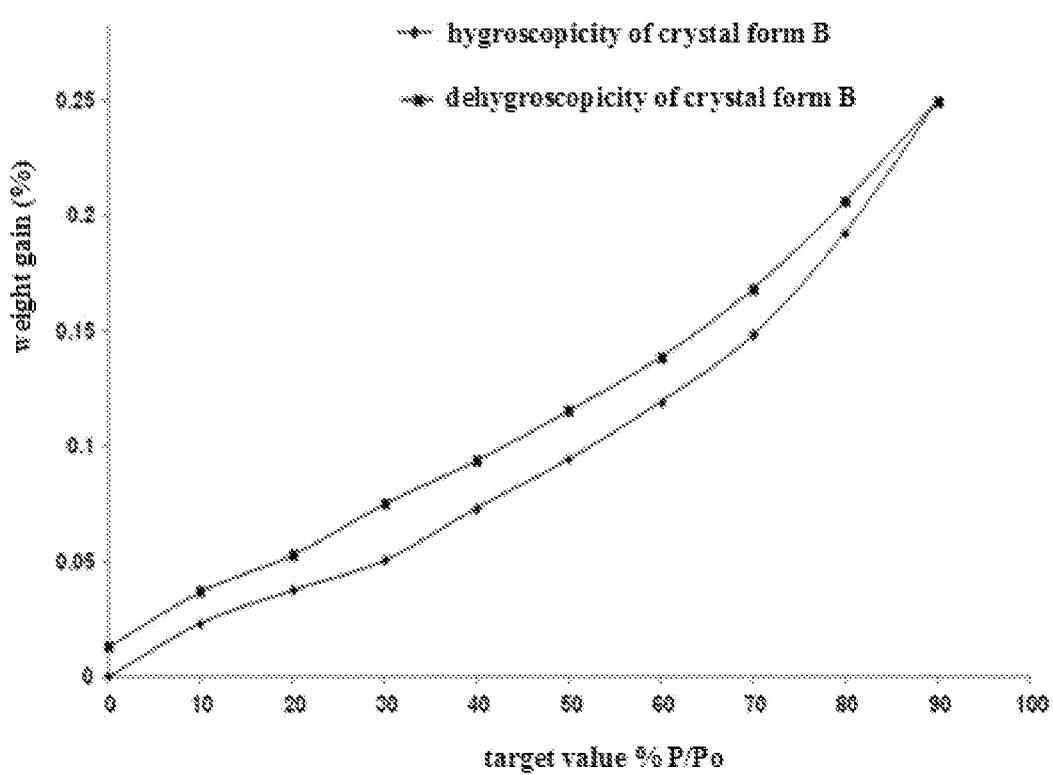
FIG. 7 is a DVS pattern of the crystal form B of the compound of Formula (I).

Experimental Materials:
SMS DVS Advantage dynamic vapor adsorption instrument
Experimental Method:
10-15 mg of the crystal form B of the compound of Formula (I) was taken and placed on a DVS sample pan for test.
Experiment Result:
The crystal form B of the compound of Formula (I) had a DVS spectrum as shown in FIG. 7. At 25° C., 80% humidity, its weight gain ΔW=0.1928%.

in Table 3) was added to start the reaction. Information about FGFR1, FGFR4 and their substrate's supplier, catalog number and lot number, as well as their concentration in the reaction solution, was listed in Table 3. After the reaction was carried out at room temperature for 120 minutes, the reaction solution was spotted on a P81 ion exchange filter paper (Whatman number 3698-915). After washing the filter paper with a 0.75% phosphoric acid solution repeatedly, the radioactivity of the phosphorylated substrate left on the filter paper was measured. The kinase activity data was expressed by comparing the kinase activity of the test compound with that of blank group (containing DMSO only), and $IC_{50}$ was determined by curve fitting with Prism4 software (Graph-Pad). The experiment results were shown in Table 4.

TABLE 3

Information about kinases, substrates and ATP for in vitro tests

| Kinase | Supplier | Catalog number | ILot number | Kinase concentration in reaction solution (nM) | ATP concentration (μM) |
|---|---|---|---|---|---|
| FGFR4 | Invitrogen | P3054 | 26967J | 2.5 | 100 |
| FGFR1 | Invitrogen | PV3146 | 28427Q | 1.75 | 5 |

| Substrate | Supplier | Catalog number | Lot number | Substrate concentration in reaction solution (μM) |
|---|---|---|---|---|
| pEY (mg/ml) + Mn | Sigma | P7244-250MG | 062K5104V | 0.2 |
| pEY (mg/ml) + Mn | Sigma | P7244-250MG | 062K5104V | 0.2 |

Experimental Conclusion:
The crystal form B of the compound of Formula (I) had a weight gain caused by moisture-adsorption of 0.1928% at 25° C. and 80% RH, indicating that the crystal form B of the compound of Formula (I) had no or almost no hygroscopicity.

Experimental Example 1: Evaluation of Inhibitory Activity of Wild Type Kinase In Vitro $IC_{50}$ was determined by using $^{33}P$ isotope-labeled kinase activity assay (Reaction Biology Corp), to evaluate the inhibitory ability of the test compound against human FGFR1 and FGFR4.
Buffer conditions: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, and 1% DMSO.
Test procedures: At room temperature, the compound of Formula (I) was dissolved in DMSO to prepare a 10 mM solution. The substrate was dissolved in a freshly prepared buffer, and added with the test kinase and well mixed. By using acoustic technology (Echo 550), the solution of the test compound in DMSO was added into the above well-mixed reaction solution, to allow a compound concentration in reaction solution to be 10 μM, 3.33 μM, 1.11 μM, 0.370 μM, 0.123 μM, 41.2 nM, 13.7 nM, 4.57 nM, 1.52 nM, and 0.508 nM, or to be 10 μM, 2.50 μM, 0.62 μM, 0.156 μM, 39.1 nM, 9.8 nM, 2.4 nM, 0.61 nM, 0.15 nM, and 0.038 nM. After 15 minutes of incubation, $^{33}P$-ATP (having an activity of 0.01 μCi/μl, and corresponding concentrations were given

TABLE 4

Results of in vitro screening test for compounds of the present disclosure

| | $IC_{50}$ (nM) | |
|---|---|---|
| Compound | FGFR1 | FGFR4 |
| reference compound 1 | 0.9 | 3.1 |
| reference compound 2 | 570 | 8754 |
| reference compound 3 | 1.7 | 17.3 |
| compound represented by Formula (I) | 0.2 | 0.2 |

Conclusion: The compound of Formula (I) in the present disclosure exhibits better inhibitory activity against wild type FGFR.

Experimental Example 2: Evaluation of Inhibitory Activity of Mutant-Type Kinase In Vitro $IC_{50}$ was determined by using $^{33}P$ isotope-labeled kinase activity assay (Reaction Biology Corp), to evaluate the inhibitory ability of the test compound against mutant FGFR. The relevant information of kinase, substrate and ATP for the in vitro test is shown in Table 5.

TABLE 5

Information about kinases, substrates and ATP for in vitro tests

| Kinase | Supplier | Catalog number | Kinase concentration in reaction solution (nM) | ATP concentration (µM) |
|---|---|---|---|---|
| FGFR2 (N549H) | Millipore | 14-742 | 0.3 | 50 |
| FGFR1 (V561M) | Signal Chem | F04-13G | 15 | 10 |
| FGFR2 (E565G) | Signal Chem | F05-12CG | 0.5 | 10 |
| FGFR2 (V564F) | SignalChem | F05-12FG | 0.3 | 20 |
| FGFR3 (V555M) | SignalChem | F06-12GG | 4 | 20 |
| FGFR3 (K650M) | Carna Biosciences | Carna 08-199 | 2 | 2.5 |
| FGFR4 (N535K) | Carna Biosciences | Carna 08-524 | 75 | 2.5 |
| FGFR4 (V550M) | Signal Chem | F07-12DG | 6 | 2.5 |

| Kinase | Substrate | Supplier | Catalog number | Substrate concentration in reaction solution (µM) |
|---|---|---|---|---|
| FGFR2 (N549H) | pEY | Sigma | P7244-250MG | 0.2 mg/mL |
| FGFR1 (V561M) | pEY + Mn | Sigma | P7244-250MG | 0.2 mg/mL |
| FGFR2 (E565G) | pEY | Sigma | P7244-250MG | 0.2 mg/mL |
| FGFR2 (V564F) | pEY | Sigma | P7244-250MG | 0.2 mg/mL |
| FGFR3 (V555M) | pEY + Mn | Sigma | P7244-250MG | 0.2 mg/mL |
| FGFR3 (K650M) | pEY + Mn | Sigma | P7244-250MG | 0.2 mg/mL |
| FGFR4 (N535K) | pEY + Mn | Sigma | P7244-250MG | 0.2 mg/mL |
| FGFR4 (V550M) | pEY + Mn | Sigma | P7244-250MG | 0.2 mg/mL |

Buffer conditions: 20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, and 1% DMSO.

Test procedures: At room temperature, test compound was dissolved in DMSO to prepare a 10 mM solution. The substrate was dissolved in a freshly prepared buffer, to which the test kinase was added and well mixed. By using acoustic technology (Echo 550), the solution of the test compound in DMSO was added into the well-mixed reaction solution, to allow a compound concentration in reaction solution to be 10 µM, 3.33 µM, 1.11 µM, 0.370 µM, 0.123 µM, 41.2 nM, 13.7 nM, 4.57 nM, 1.52 nM, 0.508 nM, or to be 10 µM, 2.50 µM, 0.62 µM, 0.156 µM, 39.1 nM, 9.8 nM, 2.4 nM, 0.61 nM, 0.15 nM, 0.038 nM. After 15 minutes of incubation, $^{33}$P-ATP (having an activity of 0.01 µCi/µl, and corresponding concentrations were given in Table 5) was added to start the reaction. Information about FGFR1, FGFR4 and their substrate's supplier, catalog number and lot number, as well as their concentration in the reaction solution, is given in Table 5. After the reaction was carried out at room temperature for 120 minutes, the reaction solution was spotted on a P81 ion exchange filter paper (Whatman number 3698-915). After washing the filter paper with a 0.75% phosphoric acid solution repeatedly, the radioactivity of the phosphorylated substrate left on the filter paper was measured. The kinase activity data was expressed by comparing the kinase activity of the test compound with that of blank group (containing DMSO only), and $IC_{50}$ was determined by curve fitting with Prism4 software (GraphPad). The experiment results are shown in Table 6.

TABLE 6

Results of in vitro screening test for compounds of the present disclosure

| Kinase | compound represented by Formula (I)(nM) |
|---|---|
| FGFR2 (N549H) | 0.5 |
| FGFR1 (V561M) | 38 |
| FGFR2 (E565G) | 0.1 |
| FGFR2 (V564F) | 33 |
| FGFR3 (V555M) | 7.3 |

TABLE 6-continued

Results of in vitro screening test for compounds of the present disclosure

| Kinase | compound represented by Formula (I)(nM) |
|---|---|
| FGFR3 (K650M) | 0.2 |
| FGFR4 (N535K) | 34 |
| FGFR4 (V550M) | 5.6 |

Conclusion: The compound of formula (I) in the present disclosure exhibits better inhibitory activity against mutant-type FGFR.

Experimental Example 3: Pharmacokinetic Investigation in Dogs

Purpose of the Experiments

The experiments aimed to test the pharmacokinetics of the test compound in beagle dogs.

Experimental Materials:

Beagle dogs(male)

Experimental Method:

Two beagle dogs were selected as one group. The compound was formulated into a designated preparation. The vehicle for intravenous injection was a mixture of DMSO: polyethylene glycol 1400 (PEG400): saline=10:40:50 (volume ratio) or a mixture of 10% DMSO/10% solutol/80% water. The vehicle for oral administration was a mixture of 0.5% methylcellulose (MC)+0.2% Tween. Each animal was given the preparation intragastrically at a predetermined dosage.

Whole blood samples, each about 500 µL, were collected from the cephalic vein or saphenous vein at 12 time points, namely 5 minutes, 15 minutes, 30 minutes, 1 hour, 2 hours, 4 hours, 6 hours, 8 hours, 12 hours and 24 hours after the animals were administered.

The plasma sample was put into a centrifuge tube containing anticoagulant, and centrifuged at 3000 g for 10 min at 4° C. The plasma supernatant was frozen quickly on dry ice, and then kept in a frige at −70±10° C. until LC-MS/MS analysis was performed.

Data Processing:

The plasma concentration of the compound was processed using a non-compartmental model by WinNonlin™ Version 6.3.0 (Pharsight, Mountain View, Calif.) pharmacokinetic software. The peak concentration ($C_{max}$), time of maximum plasma concentration ($T_{max}$), and time of the last quantifiable concentration, were determined directly from the curve of plasma concentration–time.

The following pharmacokinetic parameters: half-life time of elimination phase (T½), the mean residence time of the drug in the body from time 0 to the end timepoint (MRT0-last), the mean residence time of the drug in the body from time 0 to infinite time (MRT0-inf), area under the plasma concentration-time curve from time 0 to the end timepoint (AUC0-last), area under plasma concentration-time curve from time 0 to infinite time (AUC0-inf), were calculated using the log-linear trapezoidal method.

For the individual plasma concentration below the detection line, when it appeared before $T_{max}$, it was calculated as 0; when it appeared after $T_{max}$, it was directly excluded. All parameters and ratios were reported in the form of three significant figures.

In these experiments, the pharmacokinetic parameters were calculated based on the theoretical blood collection time and theoretical administration concentration in the embodiments. The deviation between the actual administration concentration and the theoretical concentration was within ±20%. The deviation between the actual blood collection time and the theoretical blood collection time complied with the relevant standard operating procedures (SOP) (the time points within 1 hour after administration were within ±1 minute, and the others were within 5% of the theoretical time).

Experimental Results:

The experimental results of the test compounds are shown in Table 7.

Experimental Conclusion:

Compound of Formula (I) has good pharmacokinetic indices in dogs.

The invention claimed is:

1. A compound represented by Formula (I) in crystal form

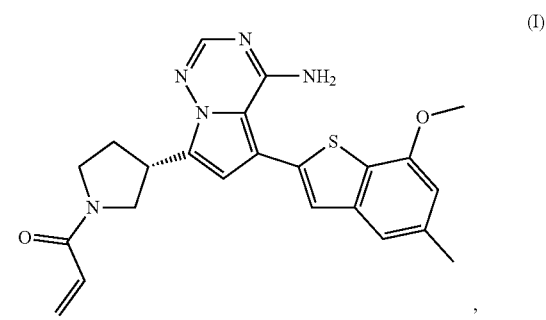 [SMILES: C=CC(=O)N1CC[C@H](c2cc(-c3cc4cc(C)cc(OC)c4s3)c3c(N)ncnn23)C1]

(I)

wherein the crystal form of the compound represented by Formula (I) is characterized by having diffraction peaks at a 2θ angle of 6.37±0.2°, 9.90±0.2°, and 19.07±0.2° in an X-ray powder diffraction pattern thereof; or the crystal form of the compound represented by Formula (I) is characterized by having diffraction peaks at a 2θ angle of 9.14±0.2°, and 15.07±0.2° in an X-ray powder diffraction pattern thereof.

TABLE 7

Pharmacokinetic investigation of the test compounds

| Test sample (compound) | Intravenous administration (1 mpk) | | | Oral administration (5 mpk) | |
|---|---|---|---|---|---|
| | Clearance (mL/min/kg) | Half-life $T_{1/2}$ (h) | Concentration integral AUC (nM · hr) | Concentration integral AUC (nM · hr) | Bioavailability F (%) |
| reference compound 1 | 17 | 0.8 | 2289 | 4668 | 41 |
| compound of Formula (I) | 9.4 | 3.0 | 4131 | 18206 | 88 |

2. A compound represented by Formula (I) in the crystal form

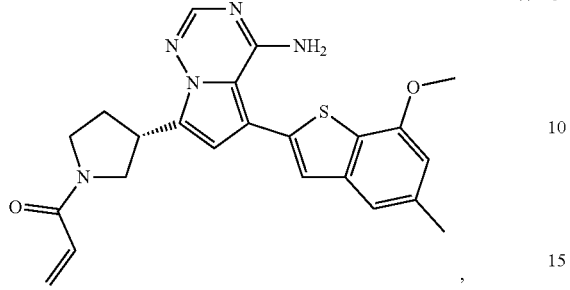

(I)

wherein the crystal form of the compound represented by Formula (I) is characterized by having diffraction peaks at a 2θ angle of 6.37±0.2°, 9.90±0.2°, 12.74±0.2°, 13.35±0.2°, 14.26±0.2°, 16.31±0.2°, 19.07±0.2°, and 21.83±0.2° in an X-ray powder diffraction pattern thereof; or the crystal form of the compound represented by Formula (I) is characterized by having diffraction peaks at a 2θ angle of 9.14±0.2°, 11.05±0.2°, 13.25±0.2°, 15.07±0.2°, 16.47±0.2° 18.31±0.2° and 22.29±0.2°.

3. A method of treating an FGFR-related disease, comprising administering the compound represented by Formula (I) in the crystal form according to claim 1 to a subject in need thereof, wherein the FGFR-related disease is a solid tumor.

* * * * *